(12) United States Patent
Barolat (10) Patent No.: US 7,769,443 B2
(45) Date of Patent: Aug. 3, 2010

(54) IMPLANTABLE REEL FOR COILING AN IMPLANTABLE ELONGATED MEMBER

(76) Inventor: Giancarlo Barolat, 730 Genesee Mountain Rd., Golden, CO (US) 80401

( * ) Notice: Subject to any disclaimer, the term of this patent is extended or adjusted under 35 U.S.C. 154(b) by 754 days.

(21) Appl. No.: 11/470,599

(22) Filed: Sep. 6, 2006

(65) Prior Publication Data

US 2008/0058876 A1    Mar. 6, 2008

(51) Int. Cl.
*A61N 1/08* (2006.01)
(52) U.S. Cl. .......................................................... 607/3
(58) Field of Classification Search ...................... 607/3
See application file for complete search history.

(56) References Cited

U.S. PATENT DOCUMENTS

| | | |
|---|---|---|
| 1,597,061 A | 8/1926 | Cultra |
| 3,195,540 A | 7/1965 | Waller |
| 3,646,940 A | 3/1972 | Timm et al. |
| 3,724,467 A | 4/1973 | Avery et al. |
| 3,796,221 A | 3/1974 | Hagfors |
| 3,822,708 A | 7/1974 | Zilber |
| 3,893,463 A | 7/1975 | Williams |
| 4,024,875 A | 5/1977 | Putzke |
| 4,219,027 A | 8/1980 | Frosch et al. |
| 4,232,679 A | 11/1980 | Schulman |
| 4,266,552 A * | 5/1981 | Dutcher et al. .............. 607/113 |
| 4,315,503 A | 2/1982 | Ryaby et al. |
| 4,379,462 A | 4/1983 | Borkan et al. |
| 4,441,498 A | 4/1984 | Nordling |
| 4,459,989 A | 7/1984 | Borkan |
| 4,549,556 A | 10/1985 | Tarjan et al. |
| 4,608,985 A | 9/1986 | Crish et al. |
| 4,934,368 A | 6/1990 | Lynch |
| 5,095,905 A | 3/1992 | Klepinski |
| 5,121,754 A | 6/1992 | Mullett |
| 5,282,468 A | 2/1994 | Klepinski |
| 5,318,572 A | 6/1994 | Helland et al. |
| 5,324,324 A | 6/1994 | Vachon et al. |
| 5,330,515 A | 7/1994 | Rutecki et al. |
| 5,376,103 A | 12/1994 | Anderson et al. |
| 5,417,719 A | 5/1995 | Hull et al. |
| 5,456,698 A * | 10/1995 | Byland et al. ................. 607/36 |
| 5,501,703 A | 3/1996 | Holsheimer et al. |
| 5,514,175 A | 5/1996 | Kim et al. |
| 5,522,874 A | 6/1996 | Gates |
| 5,571,118 A | 11/1996 | Boutos |

(Continued)

OTHER PUBLICATIONS

Disorbio et al "Assessment and Treatment of Chronic Pain"; Practical Pain Management; Mar. 2006; 10 pages.

(Continued)

*Primary Examiner*—Carl H Layno
*Assistant Examiner*—Frances P Oropeza
(74) *Attorney, Agent, or Firm*—Holme Roberts & Owen LLP (57) ABSTRACT

An implantable spool is used for spooling the excess wiring associated with a lead that extends between at least one electrode and a pulse generator of an electrical stimulation implant system. The present invention also has application to providing a spool for coiling tubing of an implantable drug delivery system. Embodiments of the invention include a method of implanting an implantable system in a body, wherein the implantable system includes a source unit and an elongated member. A method of assembling an implantable system is also described.

28 Claims, 4 Drawing Sheets

U.S. PATENT DOCUMENTS

| | | | |
|---|---|---|---|
| 5,643,330 A | 7/1997 | Holsheimer et al. | |
| 5,797,923 A | 8/1998 | Aiyar et al. | |
| 5,895,416 A | 4/1999 | Barreras et al. | |
| 5,938,690 A | 8/1999 | Law et al. | |
| 5,948,007 A | 9/1999 | Starkebaum et al. | |
| 5,957,958 A | 9/1999 | Schulman et al. | |
| 6,002,964 A | 12/1999 | Feler et al. | |
| 6,027,456 A | 2/2000 | Feler et al. | |
| 6,104,957 A | 8/2000 | Alo et al. | |
| 6,224,549 B1 | 5/2001 | Drongelen | |
| 6,246,912 B1 | 6/2001 | Sluijter et al. | |
| 6,314,325 B1 | 11/2001 | Fitz | |
| 6,345,199 B1 | 2/2002 | Thong | |
| 6,421,566 B1 | 7/2002 | Holsheimer | |
| 6,438,423 B1 | 8/2002 | Rezai et al. | |
| 6,510,332 B1 | 1/2003 | Greenstein | |
| 6,516,227 B1 | 2/2003 | Meadows et al. | |
| 6,553,263 B1 | 4/2003 | Meadows et al. | |
| 6,609,031 B1 | 8/2003 | Law et al. | |
| 6,675,046 B2 | 1/2004 | Holsheimer | |
| 6,697,676 B2 | 2/2004 | Dahl et al. | |
| 6,735,472 B2 | 5/2004 | Helland | |
| 6,885,888 B2 | 4/2005 | Rezai | |
| 6,892,097 B2 | 5/2005 | Holsheimer | |
| 6,895,280 B2 | 5/2005 | Meadows et al. | |
| 6,928,320 B2 | 8/2005 | King | |
| 6,941,171 B2 | 9/2005 | Mann et al. | |
| 6,944,507 B2 | 9/2005 | Froberg et al. | |
| 6,999,819 B2 | 2/2006 | Swoyer et al. | |
| 6,999,820 B2 | 2/2006 | Jordan | |
| 7,079,900 B2 | 7/2006 | Greenburg et al. | |
| 7,099,718 B1 | 8/2006 | Thacker et al. | |
| 7,107,097 B2 | 9/2006 | Stern et al. | |
| 7,107,104 B2 | 9/2006 | Keravel et al. | |
| 7,454,251 B2 * | 11/2008 | Rezai et al. | 607/115 |
| 2002/0111661 A1 | 8/2002 | Cross et al. | |
| 2003/0078633 A1 | 4/2003 | Firlik et al. | |
| 2003/0153959 A1 | 8/2003 | Thacker et al. | |
| 2004/0093093 A1 | 5/2004 | Andrews | |
| 2004/0127953 A1 | 7/2004 | Kilgore et al. | |
| 2004/0167584 A1 | 8/2004 | Carroll et al. | |
| 2005/0004637 A1 * | 1/2005 | Singhal et al. | 607/116 |
| 2005/0010259 A1 | 1/2005 | Gerber | |
| 2005/0055065 A1 | 3/2005 | Campbell | |
| 2005/0055779 A1 | 3/2005 | Damewood | |
| 2005/0065394 A1 | 3/2005 | Spiegel | |
| 2005/0107841 A1 | 5/2005 | Meadows et al. | |
| 2005/0119713 A1 | 6/2005 | Whitehurst et al. | |
| 2005/0148149 A1 | 7/2005 | Nabeshima | |
| 2005/0149148 A1 | 7/2005 | King | |
| 2005/0182470 A1 | 8/2005 | Cross | |
| 2005/0192644 A1 | 9/2005 | Boveja et al. | |
| 2005/0228451 A1 | 10/2005 | Jaax et al. | |
| 2005/0240242 A1 | 10/2005 | DiLorenzo | |
| 2005/0240243 A1 | 10/2005 | Barolat et al. | |
| 2006/0052826 A1 | 3/2006 | Kim et al. | |
| 2006/0052836 A1 | 3/2006 | Kim et al. | |
| 2006/0074450 A1 | 4/2006 | Boveja et al. | |
| 2006/0136008 A1 | 6/2006 | Tadlock | |
| 2006/0178718 A1 | 8/2006 | Jordan | |
| 2006/0247688 A1 * | 11/2006 | Olson et al. | 607/5 |

OTHER PUBLICATIONS

Lubenow et al.; "Advances in Neurostimulation Systems Video Presentation"; International Research Foundation for RSD/CRPS; Jul. 16, 2006; 12 pages.

* cited by examiner

Fig. 10 under the patient's skin, and may some times bulge. This can detrimentally impact patient satisfaction and can also negatively influence cooperation with the treating physician. Also, if the surgeon must replace or augment one or more components of a previously implanted system, the wiring must be dissected from tissue that has grown around its length. Accordingly, if the wiring is looped and/or otherwise awkwardly positioned, then subsequent removal of the wiring can be more difficult than a neatly situated lead. Therefore, it would be advantageous to provide a device and method for use that allows a surgeon to utilize pre-manufactured leads and organize excess length of such leads within a surgical site.

IMPLANTABLE REEL FOR COILING AN IMPLANTABLE ELONGATED MEMBER

FIELD

The present invention is related to medical implants, and more particularly, to implants comprising a material that may be coiled.

BACKGROUND

A variety of medical implants include a length of elongated material, such as tubing or wiring. For example, implanted pumps may include a length of tubing extending between the pump location and the desired delivery point, wherein the tubing serves to convey a prescribed dosage of medicine, such as pain killer, to a portion of the patient's body. As another example, electrical stimulation sources or pulse generators are used in combination with electrodes to provide electrical stimulation of nerves for the treatment of pain. As further background to existing treatment systems, reference is made to U.S. Patent Application Publication No. 2005/0010259 that discloses electrical stimulation and drug therapy systems, and the content of the aforementioned application is incorporated herein by reference in its entirety.

In general, because of its size, a pulse generator is typically separated from the electrodes that actually deliver the electrical stimulation to the target area, where the target may be the spinal cord or its peripherhal nerves, or other body locations, such as the head or legs. More particularly, a length of wiring or lead is implanted and extends between the pulse generator and the electrodes placed at the target location, wherein the electrodes are interconnected to the lead using a coupling, or alternatively, the electrodes may be integrally formed at the end of the lead itself.

Figure 1:
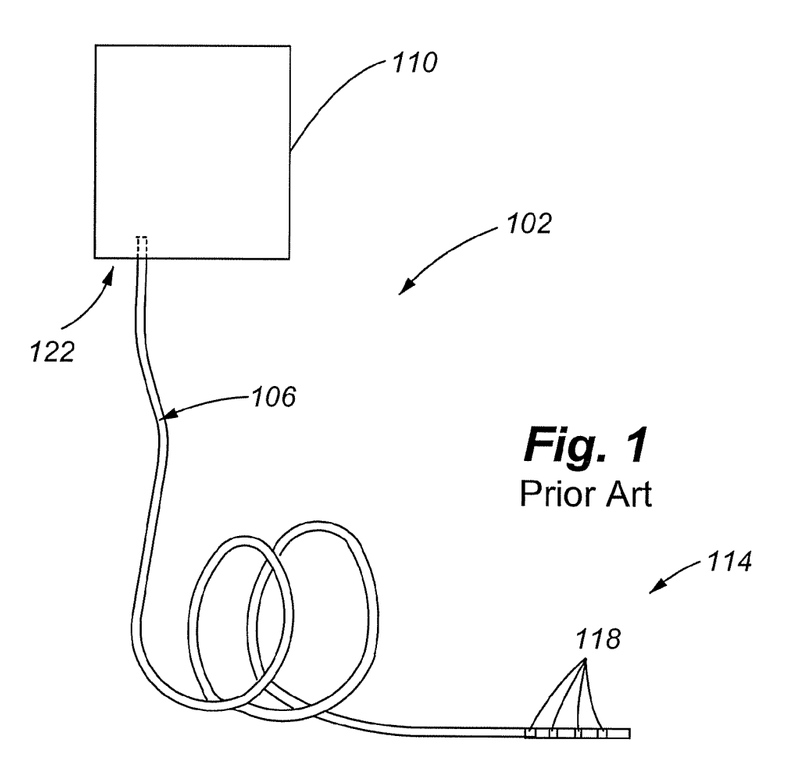
FIG. 1 is a side elevation view of an electrical stimulation system known in the prior art.

Leads typically are supplied by a medical device manufacturer, and therefore, are available pre-made and can include wiring for an electrode array. More particularly, leads typically contain a plurality of conductors leading to a coupling or corresponding number of electrodes that may be separated at the distal end of the lead. Such configuration allows electrical stimulation to be provided over an area rather than at one specific point. Referring to FIG. 1, a neurostimulator 102 is shown that includes a lead 106 and a pulse generator 110. The lead 106 has a distal end 114 that typically comprises a plurality of electrodes 118. The proximal end 122 of the lead 106 typically is adapted for mating with the pulse generator 110. Because the structure of the lead 106 has a plurality of conductors leading to a plurality of electrodes 118, a surgeon typically does not modify the length of the lead 106 because of the difficulty that would be associated with trying to splice the different conductors together. Accordingly, the surgeon typically uses the lead 106 as it is manufactured, and does not modify its length.

During the course of a surgical procedure to implant a neurostimulator 102, the surgeon will implant the pulse generator 110 in an appropriate body location, such as the upper chest, buttock or abdomen of the patient. The surgeon will also implant a lead 106 and electrode 118 and connect the lead 106 to the pulse generator 110. The surgeon chooses the length of the lead 106 based upon the patient's size and perhaps other factors, such as patient growth, but must choose a lead length that is at least long as the distance between the pulse generator 110 and the electrode target location. The excess length of the lead 106 is then typically inserted or tucked into the patient's body at one of the incision locations. As discussed further below, it is this last step that poses several problems.

One issue associated with the excess length of the lead is that, since the surgeon must essentially push the excess length into the incision, the wiring of the lead can sometimes become kinked and damaged, thereby requiring replacement. In addition, the excess length can create an unsightly appearance under the patient's skin, and may some times bulge. This can detrimentally impact patient satisfaction and can also negatively influence cooperation with the treating physician. Also, if the surgeon must replace or augment one or more components of a previously implanted system, the wiring must be dissected from tissue that has grown around its length. Accordingly, if the wiring is looped and/or otherwise awkwardly positioned, then subsequent removal of the wiring can be more difficult than a neatly situated lead. Therefore, it would be advantageous to provide a device and method for use that allows a surgeon to utilize pre-manufactured leads and organize excess length of such leads within a surgical site.

SUMMARY

The present invention addresses the shortcomings of the prior art by providing a device for spooling the excess wiring associated with a lead that extends between the electrodes and pulse generator of an electrical stimulation implant system. The present invention also has application to providing a spool for implanted tubing that is associated with, for example, an implantable drug delivery system. The present invention has application to systems that are implantable within humans, and also has application to veterinary medicine, wherein the devices and methods described herein may be used in association with treating, for example, animals, such as horses.

It is to be understood that the present invention includes a variety of different versions or embodiments, and this Summary is not meant to be limiting or all inclusive. This Summary provides some general descriptions of some of the embodiments, but may also include some more specific descriptions of certain embodiments.

As a general example, one embodiment is an implantable system that includes: (a) a source unit (such as a pulse generator for an electrical stimulation system, and/or a drug reservoir and/or fluid pump for a drug treatment system); (b) an elongated member operatively associated with the source unit (where, for example, the elongated member may be an electrical lead and/or tubing to convey a drug); and (c) a spool for receiving at least one winding of the elongated member.

It is an aspect of the present invention to provide an implantable spool for use in an implantable medical treatment system. The system has a treatment source unit and a flexible elongated member connected to the treatment source unit. The implantable spool may be spaced apart from the treatment source unit and a distal end of the flexible elongated member. The implantable spool preferably includes a core around which at least a portion of the flexible elongated member may be wound. In accordance with embodiments of the present invention, the treatment source unit may comprise a drug pump and/or a pulse generator. In accordance with embodiments of the present invention, the elongated flexible member may comprise a tubing and/or an electrical wiring lead. In accordance with embodiments of the present invention, the spool may further comprise a pair of flanges connected to the core. In accordance with embodiments of the present invention, the spool may comprise a cap covering at least a portion of a winding channel located between the pair of flanges. In accordance with embodiments of the present invention, at least a first flange of the pair of flanges may comprise a groove for receiving at least a portion of the elongated member. In accordance with at least some embodiments of the present invention, the groove is located on a tab attached to the first flange. In accordance with at least some embodiments of the present invention, the tab comprises a pair of opposing fingers oriented transverse to an outer lateral surface of the first flange. In accordance with embodiments of the present invention, one or more of the flanges may comprise an aperture adapted for receiving a suture.

As noted above, the present invention has application to both drug delivery systems and electrical stimulation systems. Thus it is an aspect of the present invention to provide an electrical stimulation system for providing electrical stimulation to an internal tissue of a patient. The system includes: an implantable pulse generator; an implantable lead operatively associated with the pulse generator; and an implantable spool adapted for receiving at least a first winding of the lead.

It is a further aspect of the invention to provide a system that allows for a variety of structures to fulfill certain functions. Thus, an implantable system for providing treatment to an internal tissue of a patient is provided. The system includes: a source unit, such as a drug pump or a pulse generator; an elongated member, such as electrical wiring or tubing; and a device for receiving at least a first winding of the elongated member.

It is also an aspect of the present invention to provide a spool that can be used in combination with other treatment components, including pre-existing components. Thus, in subcombination, an implantable spool is provided for use in an implantable system where an elongated member is to be implanted.

It is also an aspect of the present invention to provide a method of using a spool for winding at least a portion of an elongated member. Thus, in accordance with embodiments of the present invention, a method of installing a neurostimulation system in a patient is provided. The method includes:

(a) making an incision in a first tissue of the patient, the incision for placement of a pulse generator;

(b) making an incision in a second tissue of the patient, the incision for placement of at least one electrode;

(c) winding at least a portion of a lead around an inner core of a spool, the lead interconnecting the electrode(s) to the pulse generator; and (d) implanting the spool within the patient.

In addition, the method may further comprise inserting a portion of the lead into a groove, covering at least a portion of a winding channel of the spool with a cap, and/or suturing the spool to tissue of the patient. The method is also applicable to implanting a drug treatment system.

A method of assembling an implantable system is also provided. The method of assembling includes providing an implantable source unit, an implantable elongated member, and an implantable spool for receiving at least a first winding of the elongated member.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

The drawings are not necessarily to scale.

DETAILED DESCRIPTION

In accordance with embodiments of the present invention, a device is provided for organizing an implantable elongated member within a patient, wherein the elongated member may be tubing associated with a drug delivery system, or may be wiring associated with an electrical stimulation system. In general, embodiments of the present invention comprise a spool or reel used to organize the excess length of the elongated material.

Figure 2:
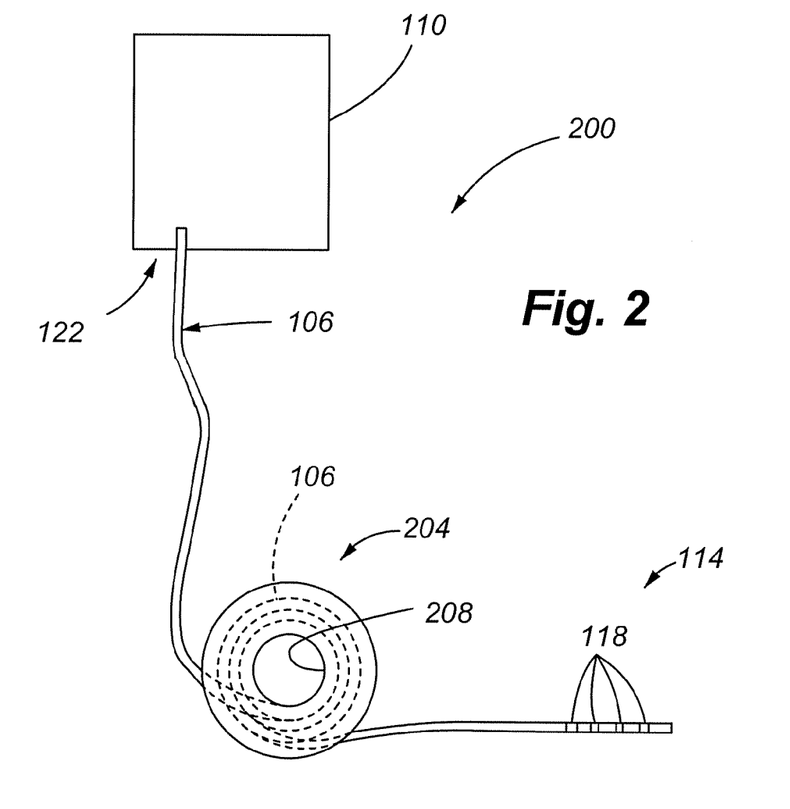
FIG. 2 is a side elevation view of an electrical stimulation system in accordance with embodiments of the present invention.

Referring now to FIG. 2, and in accordance with embodiments of the present invention, an electrical stimulation system 200 is shown. The electrical stimulation system 200 comprises a pulse generator 110, a lead 106, electrodes 118, and reel or spool 204. Although the spool 204 may have any shape, it is preferably round or oval, and includes an inner core 208 around which the excess lead 106 is wrapped.

Figure 3:
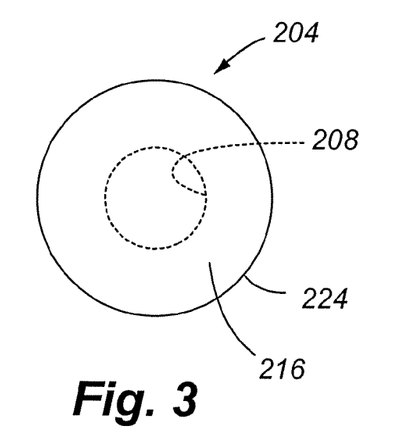
FIG. 3 is a side elevation view of the spool in accordance with at least one embodiment of the present invention.
Figure 4:
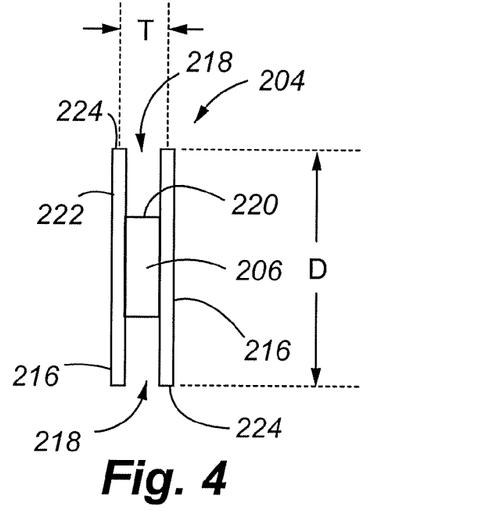
FIG. 4 is a front elevation view of the spool shown in FIG. 3.

Referring now to FIGS. 3 and 4, side and front elevation views of spool 204 are shown, respectively. In accordance with embodiments of the present invention, the spool 204 comprises first and second flanges 216 for forming a winding channel 218, thereby laterally confining the excess wiring wound within the spool 204. As noted above, the spool 204 also includes an inner core 208. The inner core is preferably sized for maintaining an acceptable radius of curvature for the lead 106, such that the lead 106 cannot be detrimentally kinked when being wrapped within the spool 204 during surgery. In accordance with embodiments of the present invention, although the spool 204 may be a variety of sizes, the spool 204 preferably comprises a diameter D between about 0.75 to 1.75 inches, and more preferably, a diameter D between about 1.0 to 1.5 inches. In addition, although its thickness may also be a variety of sizes, the spool 204 preferably comprises a thickness T of about 0.25 to 0.5 inches. The size of the spool 204 chosen by the surgeon will depend in part upon the amount of excess wiring to be wound around the spool 204, the size of the patient, the implantation location within the patient, and the nature of the wiring used as the lead 106.

The spool 204 and its inner core 208 are preferably sized for allowing space between the outer surface 220 of the inner core 208 and the circumferential edge 224 of the flange 216 so that the lead 106 may be wrapped around the inner core 208 without extending substantially beyond circumferential edge 224 of the flange 216. Of course, the spool 208 may be made and provided in a variety of sizes, thereby allowing for a greater number of windings of the lead 106 within the spool 204.

Figure 5:
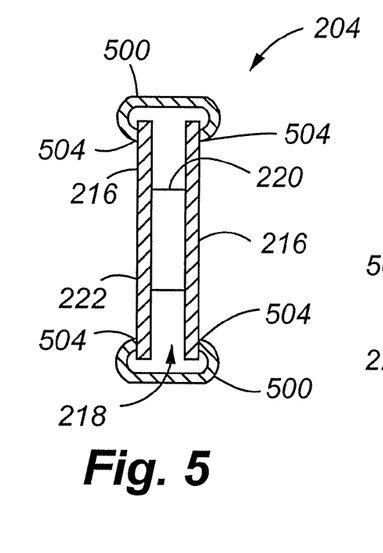
FIG. 5 is a cross-sectional view of a spool in accordance with embodiments of the present invention.
Figure 6:
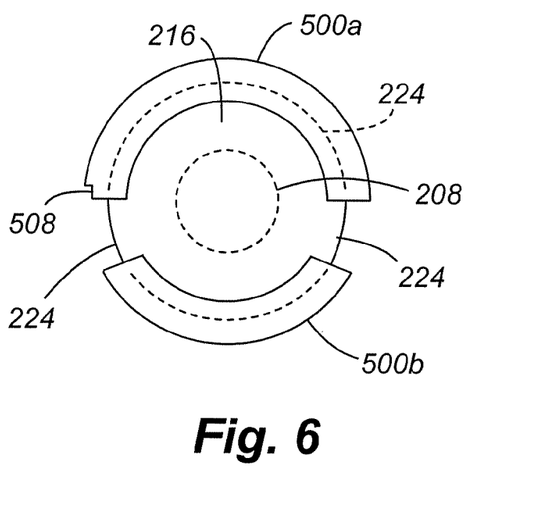
FIG. 6 is a side elevation view of the spool shown in FIG. 5.

Referring now to FIG. 5, a cross-sectional view of spool 204 is shown, in which an optional flap, covering or cap 500 is provided. The cap 500 covers at least a portion of the circumferential edge 224 of the spool 204 after the excess lead 106 is wound around the inner core 208. The cap 500 prevents tissue from growing into the area between flanges 216 after the spool 204 and lead 106 have been implanted. The cap 500 may enclose nearly the entire circumferential edge 224 of the spool 204, or it may cover only a portion of it. As shown in FIG. 6, a first cap portion 500a may be used in combination with a second cap portion 500b, wherein the use of a plurality of caps 500 allows the lead 106 to enter and exit the spool 204 at gaps between the cap portions 500a and 500b. Of course, a number of different types of coverings for the winding channel 218 are possible, and such variations are within the scope of the present invention.

The cap 500 may use a variety of ways for interconnecting to the spool 204, such as a living hinge on one its lateral edges 504 with an flange 216 of the spool 204, or it may form a friction fit at one or more of its lateral edges 504 with the outer surface 222 of the flanges 216 of the spool 204. In use, a surgeon would wind the excess lead 106 around the inner core 208 of the spool 204, and then apply the optional cap 500 at a location that does not interfere with the entry and exit of the lead 106 to the spool 204. The cap 500 may further comprise one or more openings or slits 508 sized to guide or hold the lead 106.

Figure 7:
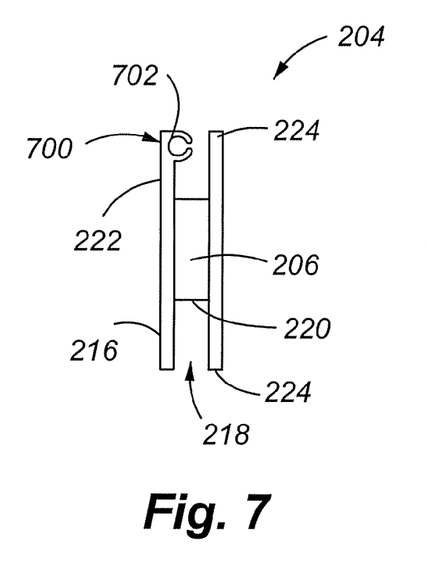
FIG. 7 is a front elevation view of a spool in accordance with embodiments of the present invention.
Figure 8:
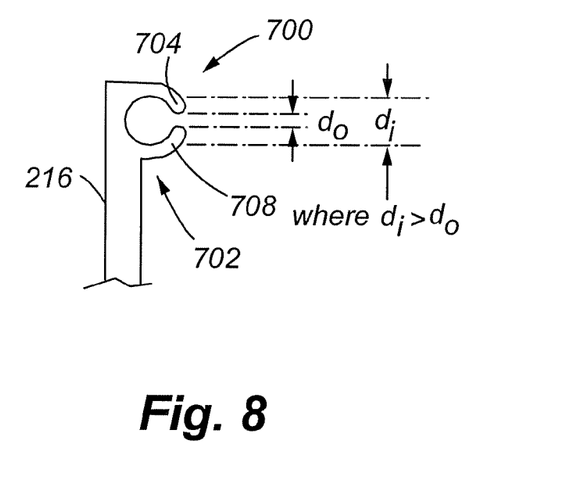
FIG. 8 is a detail view of a portion of the spool shown in FIG. 7.

Referring now to FIGS. 7 and 8, and in accordance with embodiments of the present invention, a spool 204 is shown that comprises an optional guide or groove 700 that is operatively associated with a portion of the spool 204 or its features, such as one of the flanges 216. The groove 700 serves as a receptacle for receiving a portion of the lead 106 and holding the lead in place. Thus, the natural tendency of the wound lead 106 to radially expand after winding around the inner core 208 can be resisted by use of one or more grooves 700 to hold the lead 106. Referring now to FIG. 8, an embodiment of a groove 700 is illustrated, wherein the groove 700 is formed on an inward facing tab 702 by two opposing fingers 704 and 708. In accordance with embodiments of the present invention, the fingers 704 and 708 may be oriented transverse to an outer surface 222 of an flange 216 of the spool 204. In addition, a separation distance between the fingers 704 and 708 may vary to provide a smaller opening diameter $d_o$ than an inner groove diameter $d_i$. One or more of the fingers 704 and 708 may be biased and/or flexible. Accordingly, the groove holds or receives the lead 106, and other available structures used alone or in combination include a slit in one or more of the flanges 216, and other structures, such as a clasp, a clip, an elastic member or band, etc.

Figure 9:
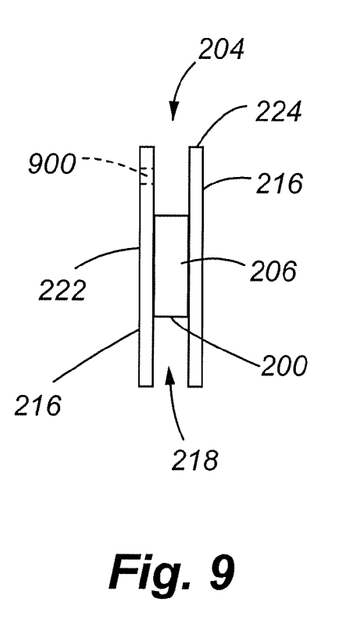
FIG. 9 is a front elevation view of a spool in accordance with embodiments of the present invention.
Figure 10:
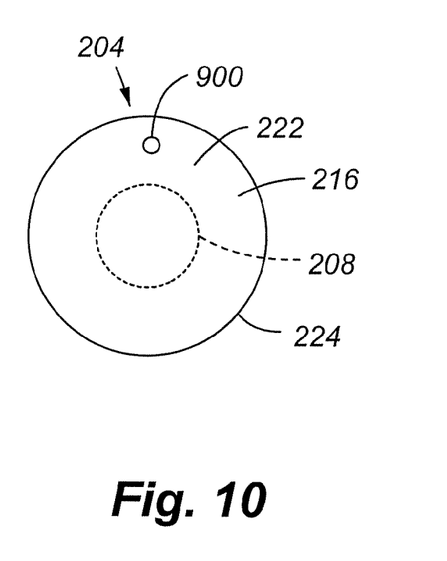
FIG. 10 is a side elevation view of the spool shown in FIG. 9.

Referring now to FIGS. 9 and 10, and in accordance with embodiments of the present invention, a spool 204 is shown that includes an optional suture aperture 900 for suturing the spool 204 to surrounding tissue at a desired implantation site. Accordingly, the suture aperture 900 provides a way to secure the spool 204 to a tissue of the patient. In addition, alternative ways of securing the spool 204 to tissue may comprise other possible structures, including a tab for receiving a staple, or a clip for tissue engagement, etc. The suture aperture 900 may be located at a variety of locations, such as through an flange 216, or on a tab operatively associated with the spool 204.

In accordance with embodiments of the present invention, the spool 204 may comprise a biasing member (not shown), wherein the spool 204 automatically releases and/or retracts a portion of the lead 106.

If desired, combinations of the features described herein may be used, such as use of a cap 500 in combination with a groove 700, or a groove 700 used in combination with a suture aperture 900.

Figure 11:
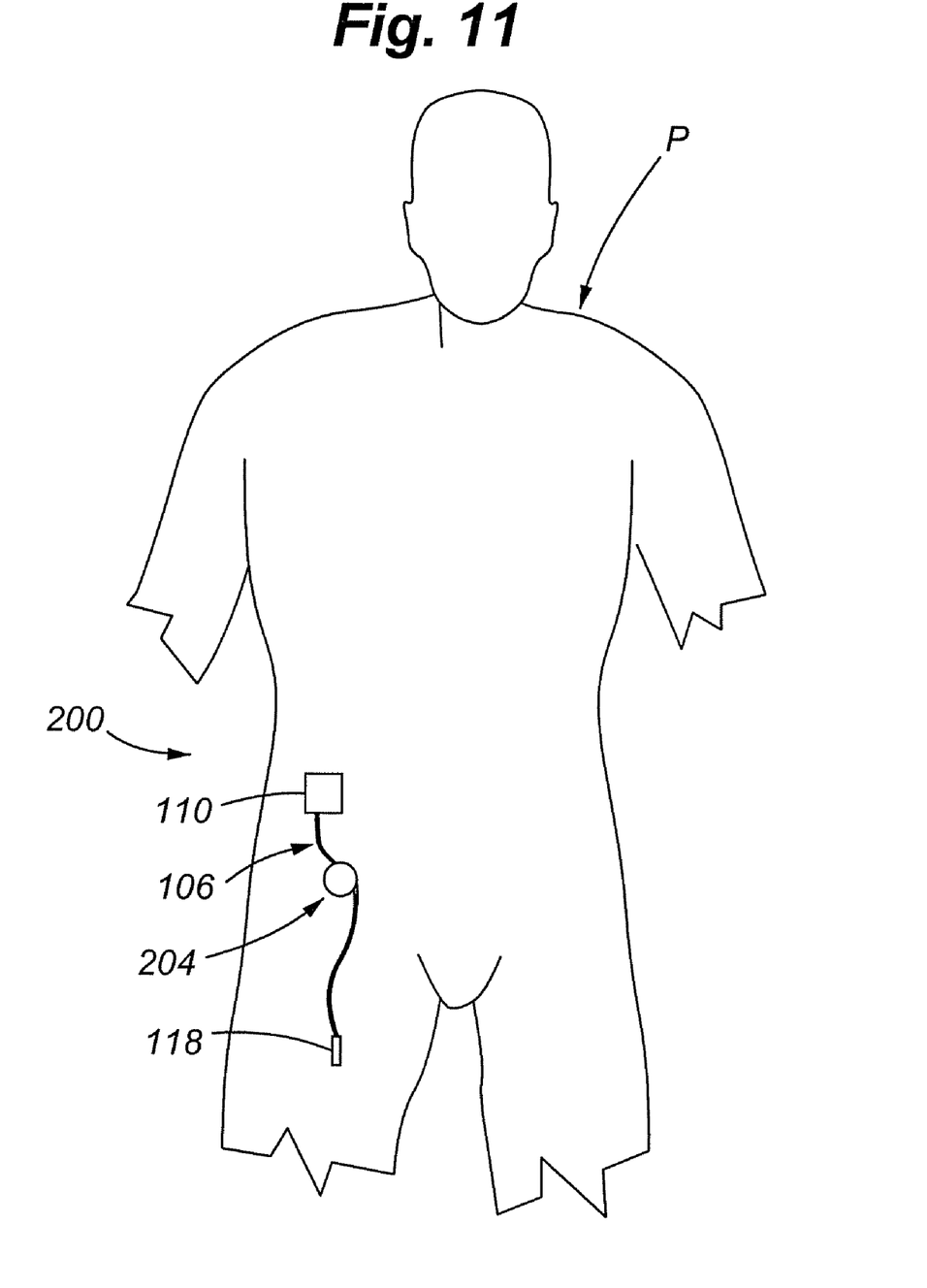
FIG. 11 is a front elevation view of a patient with a system comprising the present invention implanted into the patient.

Referring now to FIG. 11, embodiments of the present invention include a method of using the spool 204. Accordingly, in use, a surgeon first provides an incision for receiving at least the spool 204. The surgeon also winds at least a portion of the lead 106 within the spool 204 and implants the spool 204 and lead 106 within a patient P. The spool 204 is sized for being appropriate for implanting spaced apart from at least one of the pulse generator 110 and the electrodes 118, or within the vicinity of at least one of the pulse generator 110 and the electrodes 118. In accordance with embodiments of the present invention, the spool 204 may be positioned such that either the lead 106 extends in a substantially straight line between the pulse generator 110 and the location of the implanted electrodes 118, or it is alternatively positioned to accommodate the anatomy of the patient P, such as at a third location where the lead typically forms a bend between the pulse generator 110 and the location where the electrodes 118 are implanted. Optional steps associated with the method of use include inserting the lead 106 into a groove 700 that is associated with the spool 204, placing a cap 500 over at least a portion of the winding channel 218, and/or suturing the spool 204 to tissue at the spool implant location. Additional optional steps include closing the incision, causing a second incision to be made at a later time, and unwinding or winding at least a portion of the lead 106 from the spool 204.

Embodiments of the present invention further include a method of assembling an implantable system, the method comprising: providing a source unit, such as a pulse generator or drug reservoir; providing an elongated member such as an electrical lead or tubing; and providing a spool for receiving a least a first winding of the elongated member. Additional steps of the method of assembling may include providing the spool with added features, such as: a cover; a groove; and a structure associated with allowing the spool to be attached to tissue of a body.

At least portions of the spool 204 and/or its associated features may be made from one or more materials that possesses the appropriate strength characteristics necessary to withstand conditions from the body and associated implants when used in medical applications. In addition, the materials may be chosen to provide desired flexibility characteristics. In accordance with embodiments of the present invention, examples of materials that may be used to make at least portions of the spool 204 include, but are not necessarily limited to, silicone, polyether ether plastics, such as ketone (PEEK), polyether ketone ketone (PEKK), ultra high molecular weight polyethylene (UHMWPE), and polymethylmethacrylate (PMMA); metals, such as titanium and stainless steel; composites; as well as other tissue compatible materials.

While particular embodiments of the present invention have been described in some detail, it should be understood that other related embodiments are intended to be within the scope of the present invention. For example, other ways to functionally and structurally provide an implantable spooling device in combination with an elongated member, such as tubing or electrical wiring, are encompassed by the present invention, whether such structures employ flanges and/or an inner core, and/or whether such structures are integrally made or form a connectable part of the elongated member itself or another implantable member, and/or whether such structures include other features that are well within the knowledge of those of ordinary skill in this art, and/or whether such structures are conventional structures or those that may be developed in the future. In particular, however, other implantable reels or spool mechanisms, including those that may comprise a biasing member or auto-wind/rewind capability are considered within the scope of the invention. Furthermore, such devices may include adaptations of pumps or pulse generator units, and/or couplings, and/or tubing, and/or electrical leads, and/or exit orifices, and/or electrode arrays.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. An implantable system for implanting into a patient, the implantable system comprising:
   an implantable source unit;
   an implantable elongated member operatively associated with said implantable source unit;
   an implantable spool adapted for receiving multiple windings of said implantable elongated member; and
   a first cap portion covering a first circumferential edge portion of the implantable spool, a second cap portion covering a second circumferential edge portion of the implantable spool, the first cap portion being circumferentially separated from the second cap portion by a pair of gaps, wherein the implantable elongated member enters the implantable spool at a first gap of the pair gaps and exits the implantable spool at a second gap of the pair of gaps, and wherein the first cap portion and the second cap portion radially enclose portions of a winding channel of the implantable spool.

2. The implantable system as claimed in claim 1, wherein the implantable source unit comprises at least one of a pulse generator and a drug reservoir.

3. The implantable system as claimed in claim 1, wherein the implantable source unit provides least one of a drug and an electrical stimulation to an internal tissue of the patient.

4. The implantable system as claimed in claim 1, wherein the implantable elongated member comprises at least one of an implantable lead and an implantable tubing.

5. The implantable system as claimed in claim 1, further comprising at least one implantable electrode operatively associated with said implantable elongated member.

6. The implantable system as claimed in claim 1, wherein said implantable spool comprises an aperture adapted for receiving a suture.

7. The implantable system as claimed in claim 1, wherein said implantable spool comprises at least a first flange, and wherein said first flange comprises at least one groove for receiving at least a portion of said implantable elongated member.

8. The implantable system as claimed in claim 7, wherein said groove is located on a tab attached to said first flange.

9. The implantable system as claimed in claim 8, wherein said tab comprises a pair of opposing fingers oriented transverse to an outer lateral surface of said first flange.

10. The implantable system as claimed in claim 1, wherein at least one of the first cap portion and the second cap portion frictionally engage the implantable spool.

11. The implantable system as claimed in claim 1, wherein at least one of the first cap portion and the second cap portion are connected to the implantable spool by a living hinge.

12. In subcombination, an implantable spool for use in an implantable system, the implantable system including an implantable source unit, the implantable source unit including at least one of (a) a pulse generator, and (b) a drug reservoir, the implantable system further including an implantable elongated member connected or interconnectable to the implantable source unit, wherein the implantable elongated member includes a distal end, the implantable spool for placement within a patient at a location spaced apart from at least one of (a) a location of the implantable source unit and (b) a location of the distal end of the implantable elongated member, the implantable spool comprising:
   a pair of flanges operatively connected to an inner core, wherein the inner core is adapted for receiving at least a first winding of the implantable elongated member; and
   a first cap portion covering a first circumferential edge portion of the pair of flanges of the implantable spool, a second cap portion covering a second circumferential edge portion of the pair of flanges of the implantable spool, the first cap portion being circumferentially separated from the second cap portion by a pair of gaps, wherein the implantable elongated member enters the implantable spool at a first gap of the pair gaps and exits the implantable spool at a second gap of the pair of gaps, and wherein the first cap portion and the second cap portion radially enclose portions of a winding channel of the implantable spool.

13. The subcombination as claimed in claim 12, wherein the implantable spool comprises a cap covering at least a portion of a winding channel located between said pair of flanges.

14. The subcombination as claimed in claim 12, wherein at least a first flange of said pair of flanges comprises at least one groove for receiving at least a portion of the implantable elongated member.

15. The subcombination as claimed in claim 14, wherein said at least one groove is located on a tab attached to said first flange.

16. The subcombination as claimed in claim 15, wherein said tab comprises a pair of opposing fingers oriented transverse to an outer lateral surface of said first flange.

17. The subcombination as claimed in claim 12, wherein at least one of said flanges comprises an aperture adapted for receiving a suture.

18. An implantable system for implanting into a patient, the implantable system comprising:
- an implantable source unit;
- an implantable elongated member operatively associated with said implantable source unit;
- means for receiving at least a first winding of said implantable elongated member, wherein said means for receiving is implantable and is adapted for implantation spaced apart from both of said implantable source unit and a distal end of said implantable elongated member; and
- a first and second means for radially covering a first and second circumferential edge portion of the means for receiving, the first and second means for radially covering being circumferentially separated by a pair of gaps, wherein the implantable elongated member enters the means for receiving at a first gap of the pair gaps and exits the means for receiving at a second gap of the pair of gaps.

19. The implantable system as claimed in claim 18, wherein said means for receiving comprises a spool.

20. The implantable system as claimed in claim 18, wherein said means for receiving comprises a means for securing the means for receiving to a tissue of the patient.

21. The implantable system as claimed in claim 20, wherein said means for securing comprises and aperture for receiving a suture.

22. The implantable system as claimed in claim 18, wherein said means for receiving comprises a means for holding at least a portion of said implantable elongated member.

23. The implantable system as claimed in claim 22, wherein said means for holding comprises a groove adapted for at least partially circumscribing at least a portion of a circumference of the implantable elongated member.

24. The implantable system as claimed in claim 23, wherein said means for holding comprises a tab having two opposing fingers forming said groove.

25. The implantable system as claimed in claim 18, wherein said implantable source unit comprises at least one of (a) a pulse generator, and (b) a drug reservoir.

26. The implantable system as claimed in claim 18, wherein said implantable elongated member comprises at least one of (a) an electrical lead, and (b) a tubing.

27. The implantable system as claimed in claim 18, wherein at least one of the first and second means for radially covering frictionally engage the means for receiving.

28. The implantable system as claimed in claim 18, wherein at least one of the first and second means for radially covering are connected to the means for receiving by a living hinge.

* * * * *